(12) United States Patent
Agyapong et al.

(10) Patent No.: US 6,740,070 B2
(45) Date of Patent: May 25, 2004

(54) PROTECTION AND COMFORT TAMPON

(75) Inventors: Raymond Kusi Agyapong, Cincinnati, OH (US); Lisa Ann Mackay, Cincinnati, OH (US); Dannette ReNee Adams, Independence, KY (US); David Joseph Caracci, Evendale, OH (US); Alan Lawrence Maingot, Cincinnati, OH (US); Eric Patton Weinberger, Fairfield, OH (US); Kenyata JeMauld Martin, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 218 days.

(21) Appl. No.: 10/039,979

(22) Filed: Oct. 24, 2001

(65) Prior Publication Data

US 2002/0133133 A1 Sep. 19, 2002

Related U.S. Application Data

(63) Continuation-in-part of application No. 09/695,552, filed on Oct. 24, 2000, now Pat. No. 6,554,814, which is a continuation-in-part of application No. 09/309,467, filed on May 10, 1999, now Pat. No. 6,258,075.

(51) Int. Cl.$^7$ ................................................ A61F 13/20
(52) U.S. Cl. ............................ 604/385.18; 604/385.17; 604/11
(58) Field of Search ..................... 604/363, 385.18, 604/904, 385.17, 11–18

(56) References Cited

U.S. PATENT DOCUMENTS

| | | |
|---|---|---|
| 1,731,665 A | 10/1929 | Huebsch |
| 1,964,911 A | 7/1934 | Haas |
| 2,123,750 A | 7/1938 | Schulz |
| 2,412,391 A | 12/1946 | Crockford |
| 2,464,310 A | 3/1949 | Harwood |
| 2,566,190 A | 8/1951 | Greiner |
| 3,013,558 A | 12/1961 | Leupoid |
| 3,037,506 A | 6/1962 | Penska |
| 3,058,469 A | 10/1962 | Crockford |
| 3,101,714 A | 8/1963 | Penska |
| 3,135,262 A | 6/1964 | Kobler |
| 3,420,234 A | 1/1969 | Phelps |
| 3,572,341 A | 3/1971 | Glassman |
| 3,674,029 A | 7/1972 | Bates |
| 3,732,866 A | 5/1973 | Accavallo |
| 3,854,481 A | 12/1974 | Messing |
| 3,905,372 A | 9/1975 | Denkinger |
| 3,948,257 A | 4/1976 | Bossak |
| 3,965,905 A | 6/1976 | Schoenholz |
| 3,995,636 A | 12/1976 | Murray |
| 4,077,408 A | 3/1978 | Murray |
| 4,217,900 A | 8/1980 | Wiegner |
| 4,326,527 A | 4/1982 | Wollangk et al. |
| 4,536,178 A | 8/1985 | Lichstein et al. |
| 5,047,024 A | 9/1991 | Glassman |
| 5,112,348 A | 5/1992 | Glassman |
| 5,659,934 A * | 8/1997 | Jessup et al. |
| 5,718,675 A | 2/1998 | Leijd |
| 5,800,338 A | 9/1998 | Kollerup |
| 6,039,716 A | 3/2000 | Jessup et al. |
| 6,142,984 A | 11/2000 | Brown et al. |
| 6,433,246 B1 * | 8/2002 | Nguyen et al. |

FOREIGN PATENT DOCUMENTS

| | | |
|---|---|---|
| DE | 296 15 883 U1 | 4/1997 |
| EP | 1 064 901 A2 | 1/2001 |
| JP | 61-073317 | 5/1986 |
| JP | 2-28900 | 8/1990 |

* cited by examiner

Primary Examiner—Kim M. Lewis
Assistant Examiner—Jacqueline F Stephens
(74) Attorney, Agent, or Firm—Ingrid N. Hickman; Kevin C. Johnson

(57) ABSTRACT

Catamenial tampons having particularly desired expansion force characteristics are shown. The tampons comprise a mass of absorbent material which is fluid expanding. The tampons exert an X Dimension Force of at least about 400 grams, and a Z Dimension Force of less than about 200 grams. Alternatively, the ratio of the X Dimension Force to the Z Dimension Force is from about 10 to about 50.

20 Claims, 4 Drawing Sheets

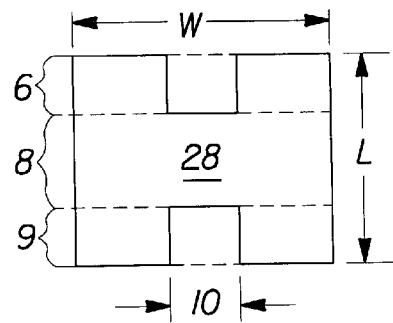
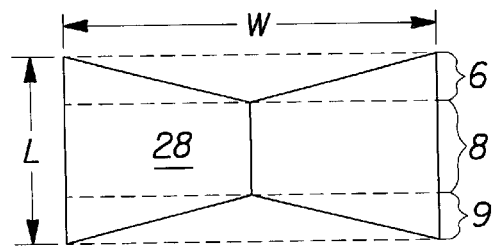
Fig. 4　　　　Fig. 5
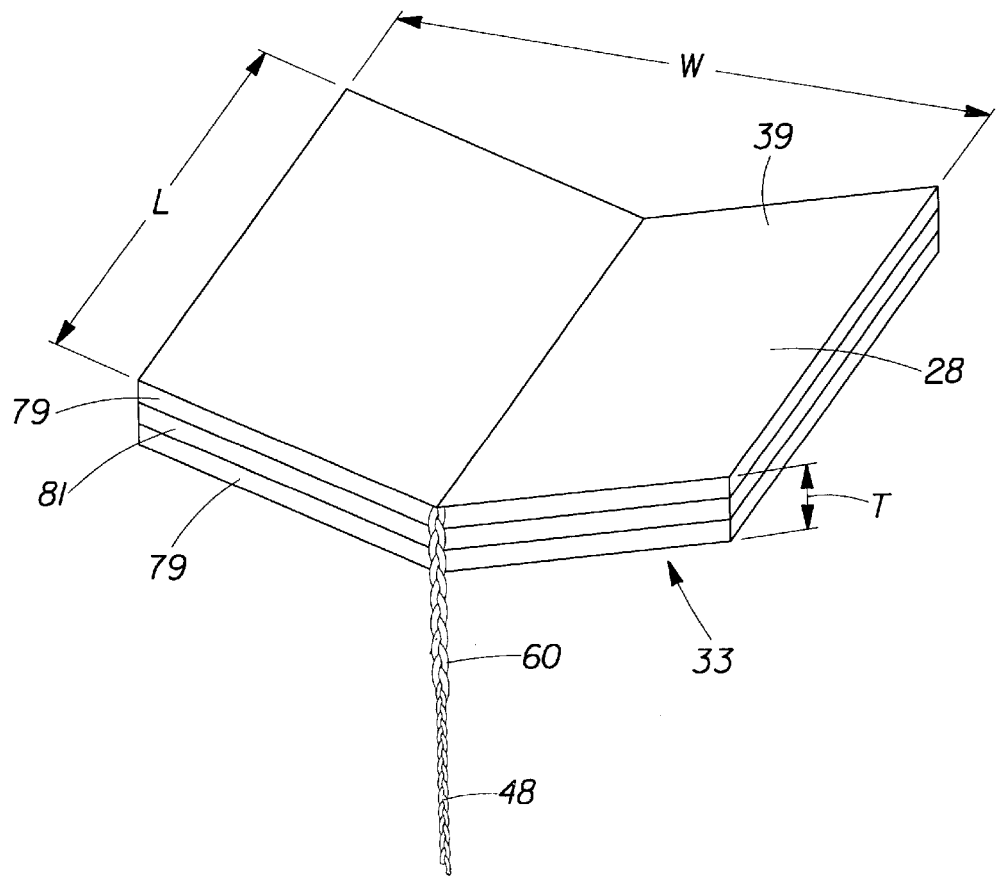
Fig. 6

PROTECTION AND COMFORT TAMPON

CROSS REFERENCE TO RELATED APPLICATIONS

This continuation-in-part of U.S. application Ser. No. 09/695,552, filed Oct. 24, 2000, now U.S. Pat. No. 6,554,814; which is a continuation-in-part of U.S. application Ser. No. 09/309,467, filed May 10, 1999, now U.S. Pat. No. 6,258,075.

FIELD OF THE INVENTION

This invention relates to absorbent tampons. More particularly, the invention relates to a tampon having improved leakage protection and comfort through improved expansion characteristics.

BACKGROUND OF THE INVENTION

A wide variety of absorbent catamenial tampons have long been known in the art. Most currently commercially available tampons are made from a tampon pledget which has been compressed into a substantially cylindrical form. Tampon pledgets of a variety of types and constructions have been described in the art. Prior to compression, the tampon may be rolled, spirally wound, folded, or assembled as a rectangular pad of absorbent material. Tampons made from a generally rectangular pledget of absorbent material have been popular and successful in the market.

The absorbent catamenial tampons now in use are typically formed from batts larger in size than the vaginal orifice, which are then compressed into a rigid cylindrical pledget in order to facilitate insertion. As fluid is absorbed, these compressed tampons are expected to re-expand toward their original pre-compressed size, and to eventually become large enough to effectively cover the vaginal cavity against fluid leakage or bypass. While it has been found that these compressed tampons perform their intended function tolerably well, even the best of them do not always re-expand sufficiently to provide good coverage against leakage while providing comfortable wear.

A compressed tampon, to perform well, should re-expand with enough force to provide the best possible anatomical fit. Nevertheless, these needs are not always consistent with the desire to provide a tampon which is comfortable to the wearer. It has been long recognized that the internal vaginal cavity in its normal collapsed state is wider in its transverse dimension than in its anterior/posterior dimension. Additionally, nerve sensitivity is higher in the anterior/posterior dimension than in the transverse dimension. Thus, it is desirable when considering a tampon for catamenial use, to provide a structure which expands enough (with sufficient force), particularly in the transverse dimension, to contact substantially all of surface of the vaginal walls from one side to the other in the vaginal cavity to prevent early bypass of the menstrual discharges from the cervix. It is also desirable to provide a comfortable tampon which provides the minimal necessary force in the anterior/posterior dimension to maintain acceptable comfort.

Prior art tampons, therefore, attempted to balance these design objectives as best as possible, often having to trade some performance with respect to one objective for improved performance with respect to another. Many currently marketed tampons, particularly rolled or spiral wound which are then compressed radially (i.e. compressed from the sides essentially uniformly in all dimensions) expand with the same transverse dimension force as anterior/posterior dimension force. These tampons do not advantageously leverage the anatomical differences of the vaginal cavity to provide maximum protection with maximum comfort since increasing the expansion forces in one dimension necessarily increases the expansion forces in the other dimension. Even those currently marketed tampons which exhibit transverse dimension forces which are greater than the anterior/posterior dimension forces may not always expand sufficiently, particularly in the transverse dimension, to provide superior coverage.

It is, therefore, desirable to provide a tampon with an improved balance of expansion force characteristics. Such a tampon should not introduce new drawbacks, such as a decreased comfort while wearing the tampon or decreased ability to comfortably remove the tampon. Ideally, such a tampon should be able to be manufactured out of materials similar to those currently used for tampons. These materials have the advantages of a proven record of suitability for human use, acceptable cost, and the ability to be manufactured into tampons without undue modifications to current commercially available manufacturing equipment.

SUMMARY OF THE INVENTION

This invention relates to catamenial tampons, and more particularly, to tampons having particularly desired expansion force characteristics. The tampons of the present invention comprise a mass of absorbent material which is fluid expanding. The tampons exert an X Dimension Force of at least about 400 grams, and a Z Dimension Force of less than about 200 grams. Alternatively, the ratio of the X Dimension Force to the Z Dimension Force is from about 5 to about 50.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

FIG. 4 is a front view of an alternative shape for a tampon pledget.

FIG. 5 is a front view of another alternative shape for a tampon pledget.

FIG. 6 is a perspective view of the tampon pledget shown in FIG. 2 which shows the layers of such pledget.

DETAILED DESCRIPTION OF THE INVENTION

Figure 1:
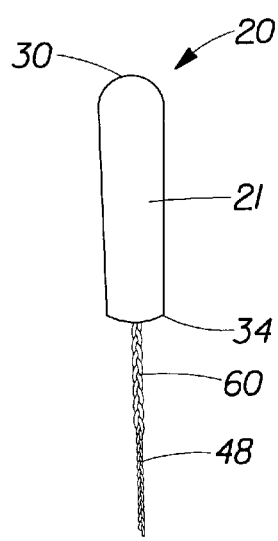
FIG. 1 is a front view of a tampon of the present invention.

The present invention is directed to an absorbent tampon having improved leakage protection and comfort characteristics. FIG. 1 shows one embodiment of such an absorbent tampon, tampon 20. The present invention, however, is not limited to a structure having the particular configuration shown in the drawings.

As used herein the term "tampon" refers to any type of absorbent structure which is inserted into the vaginal canal or other body cavities for the absorption of fluid therefrom. Typically, tampons are constructed from an absorbent material which has been compressed in any or all of the width direction, the radial direction, and the axial direction, in order to provide a tampon which is of a size and stability to allow insertion within the vagina or other body cavity. A tampon which has been so compressed is referred to herein as a "self-sustaining" form. That is, the degree of compression applied to the absorbent material of the tampon pledget is sufficient so that in the subsequent absence of external forces, the resulting tampon will tend to retain its general shape and size.

It will be understood by one of skill in the art that this self-sustaining form need not, and preferably does not persist during actual use of the tampon. That is once the tampon is inserted and begins to acquire fluid, the tampon will begin to expand and may lose its self-sustaining form. Preferably, tampons constructed according to the present invention are fluid expanding. As used herein, the term "fluid expanding" means that the tampon which has been compressed to a self sustaining form will expand or uncompress upon contact with fluid such as bodily fluids. Fluid expanding tampons are contrasted to "mechanically expanding" tampons which are tampons which use springs, or some other mechanical supplier of force to expand. An example of such a mechanically expanding tampon is described in U.S. Pat. No. 3,706,311 to Kohx et al.

As used herein the terms "pledget" or "tampon pledget" are intended to be interchangeable and refer to a construction of absorbent material prior to the compression of such construction into a tampon as described above. Tampon pledgets are sometimes referred to as a tampon blank, or a softwind, and the term "pledget" is intended to include such terms as well. In general in this specification, the term "tampon" is used to refer to a finished tampon after the compression process referred to above. It will be recognized by those of skill in the art that in some contexts these terms are interchangeable. The different stages of tampon manufacture are described herein with an eye toward providing the greatest possible clarity. Therefore, the terms used are to assist the reader in best understanding the features of the invention and not to introduce limitations in the terms not consistent with the context in which they are used in this specification.

As used herein the terms "vaginal cavity," "within the vagina", "vaginal canal", and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally are not included within the term "vaginal cavity" as used herein. The term "anterior/posterior dimension" is intended to identify the space running from the anterior wall of the vagina (the bladder side which is in the front) to the posterior wall of the vagina (the rectum side which is in back). The term "transverse dimension" is intended to identify the space which generally runs from side to side (left to right) in the vaginal cavity.

The abbreviation "gsm" as used herein is "grams per square meter". The abbreviation "mm" is millimeter.

The primary absorbent member 21 (sometimes also referred to as the "absorbent core") of the tampon 20 shown in FIG. 1 has an insertion end 30 and a withdrawal end 34. The primary absorbent member 21 may be compressed into a generally cylindrical configuration in the width direction, the radial direction, the axial direction, or in any combination of these directions. Preferably, the greatest compression of the primary absorbent member 21 takes place in the width direction. Head formation of the finished tampon is preferably accomplished by subsequent (and less substantial vs. widthwise direction) compression in the axial direction.

While the primary absorbent member 21 is preferably compressed into a substantially cylindrical configuration, other shapes are also possible. These may include shapes having a cross section which may be described as rectangular, triangular, trapezoidal, semi-circular, or other suitable shapes.

Figure 2:
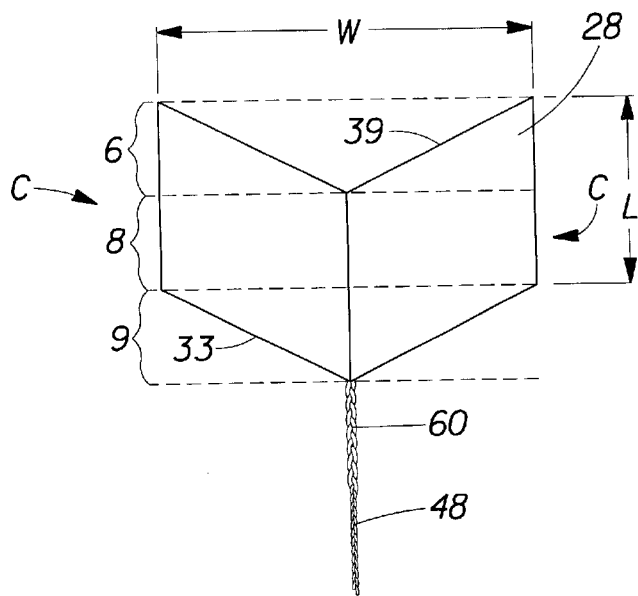
FIG. 2 is a front view of a tampon pledget from which a tampon of the present invention may be made by suitable compression.

The primary absorbent member 21 of the tampon 20 of the present invention may be formed from any suitable tampon pledget, such as tampon pledget 28 shown in FIG. 2. The tampon pledget 28 and, consequently, the finished tampon 20 may also be provided with an optional secondary absorbent material, such as secondary absorbent material 60. The tampon pledget 28 portion of the tampon 20 which will be compressed to form the primary absorbent member 21 may be any suitable shape, size, material, or construction. In the embodiment shown in FIG. 2, pledget 28 is a batt of absorbent material which is a generally "chevron shaped" pad of absorbent material. The pledget 28, has a width W and a length L. The thickness of the pledget is perpendicular to both the width W and the length L, and is the direction represented as thickness T in FIG. 6. Preferably, each of the width W, and length L, exceed the thickness T resulting in a pledget 28 which is generally in the shape of "flat sewn pad" prior to compression.

Figure 3:
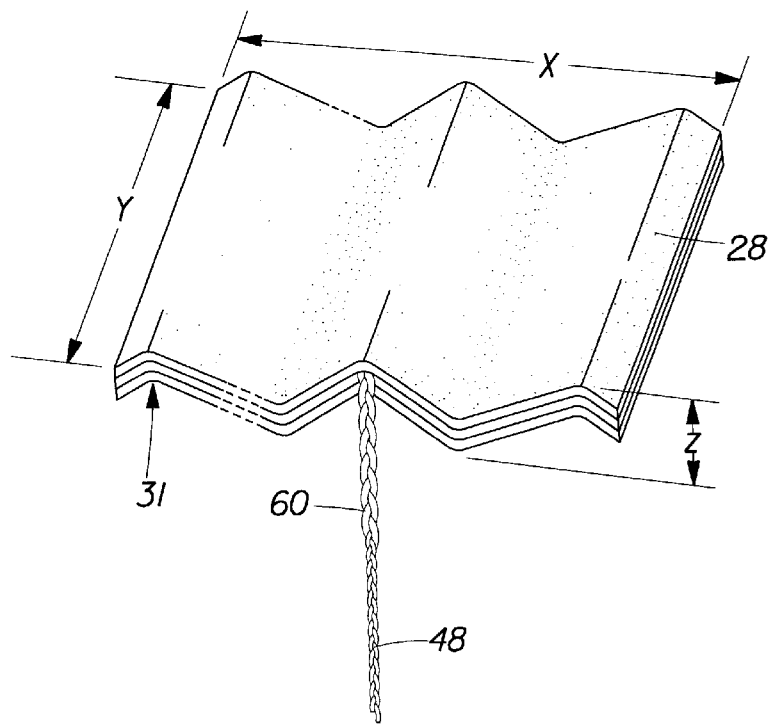
FIG. 3 is a side view of a tampon pledget in a semi-compressed state.

The tampon pledget 28 may be compressed in any manner suitable to form a primary absorbent member 21 of the present invention providing the desired X expansion forces and Z expansion forces when subjected to the Expansion Force Test set forth in the Test Method section herein. FIG. 3 shows a tampon pledget 30, of folded structure, in a semi-compressed state, wherein the compression involves a series of folds 31. This semi-compressed state depicts the tampon pledget 30 as it appears prior to complete compression and as it appears when initially expanding from a completely compressed state upon fluid acquisition. FIG. 3 shows a tampon oriented on X, Y, and Z axes. The X axis corresponds to the width of the pledget. The Y axis corresponds to the length, and the Z corresponds to the thickness of the pledget. These axes define planes which will be useful in describing the tampon forces discussed herein. The "Z plane" is the plane defined by the X and Y axes. The "Z plane" moves along the Z axis with expansion of the tampon. The Y and Z axes define the "X plane", which moves along the X axis as the tampon expands. As the tampon expands, it exerts forces. More particularly, the moving "X plane" of the tampon exerts a force in the X dimension (along the X axis of the tampon). Similarly, the moving "Z plane" exerts a force in the Z dimension (along the Z axis of the tampon).

It is believed that upon acquisition of fluid, a compressed tampon according to the present invention actually "flips" in the body of the user to orient the expanding tampon such that the X plane of the expanding tampon, which runs parallel the width W as shown in FIG. 2, situates itself with the transverse dimension of the vaginal canal. The Z plane of the expanding tampon, which corresponds to the thickness T shown in FIG. 6, situates itself with the anterior/posterior dimension of the vaginal canal. While not intending to be bound by theory, it is believed that this flipping phenomenon occurs due to the different forces needed to deform the vaginal canal, where the force to deform the vaginal canal in the anterior/posterior dimension is greater than the forces needed to deform the vaginal canal in the transverse dimension, and therefore, the tampon self orients itself with its greatest expansion force dimension oriented with the transverse dimension, taking the path of least resistance.

While the pledget 28 shown in FIG. 2 is generally chevron shaped, and the pledget 30 shown in FIG. 3 is rectangular shaped, other shapes such as trapezoidal, triangular, and semi-circular are also acceptable. Preferably, the pledget 28 may be divided into three regions, top region 6, middle region 8, and bottom region 9. In preferred embodiments, the pledget 28 is shaped such that the middle region 8 is a region having more absorbent material than the top region 6 or the bottom region 9. As shown in FIG. 2, the chevron shape of pledget 28 provides such a variation in absorbent material amounts. Other shapes which also tend to produce this variation are also possible. For example, the pledget may be generally "H" shaped, such as shown in FIG. 4. The length L and width W are depicted as is the gap width 10. A "bow tie" shape such as is shown in FIG. 5 is also suitable. While a chevron shaped pledget 28 is suitable, the edges of the chevron may be somewhat "rounded off" in order to facilitate high speed manufacturing operations. A tampon pledget of the present invention may have a uniform shape such as a rectangular shaped pledget 30 in FIG. 3, but vary in absorbent material density or thickness along the axial extent of the pledget.

In preferred embodiments, the pledget 28 may be a laminar structure comprised of integral or discrete layers. As is shown more clearly in FIG. 6, the pledget 28 may comprise outer layers 79 and at least one intermediate layer 81 positioned between the outer layers 79. In other embodiments, the pad need not have a layered structure at all.

Figure 7:
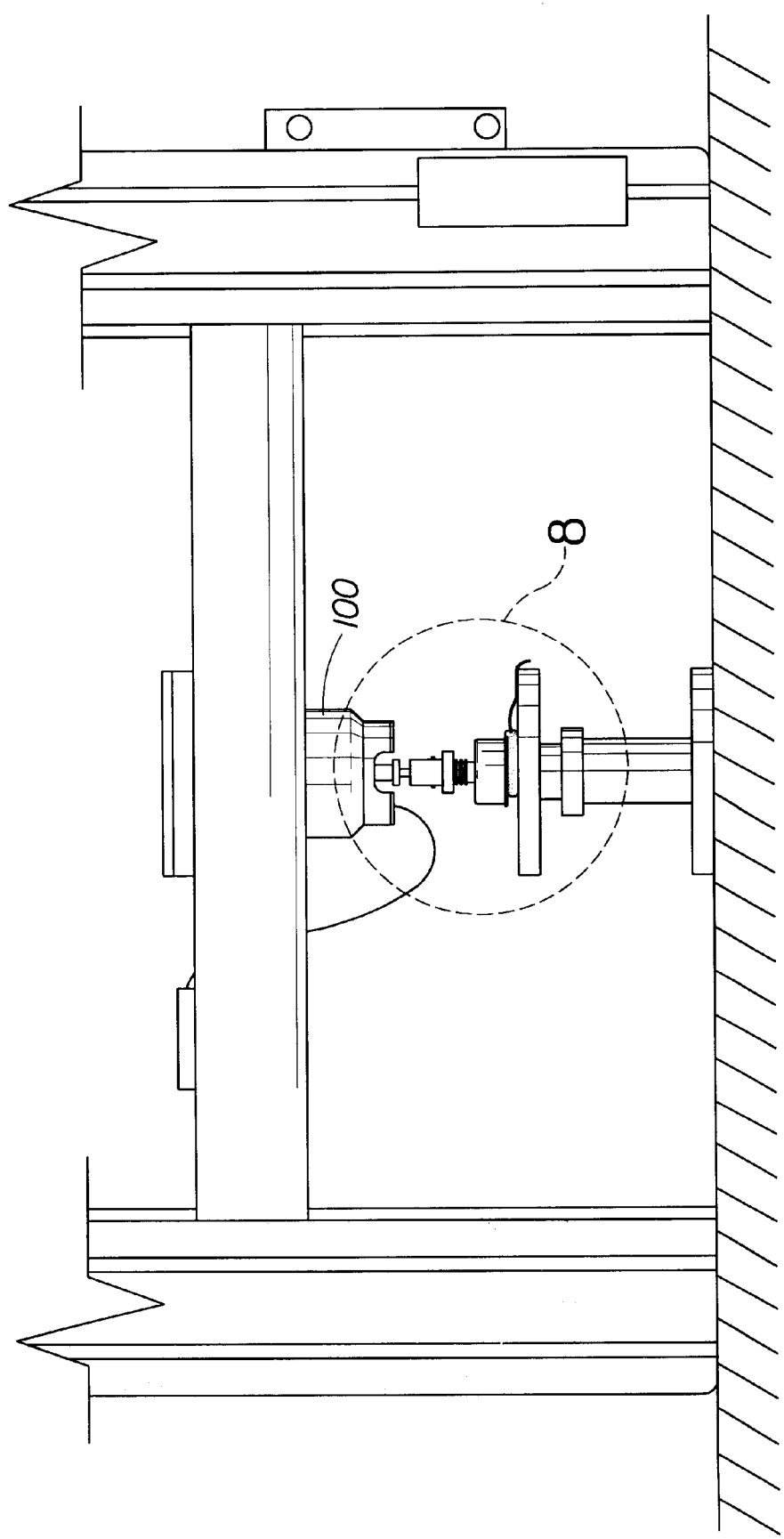
FIG. 7 is the front view of the apparatus used to conduct the Expansion Force Test described in this specification.
Figure 8:
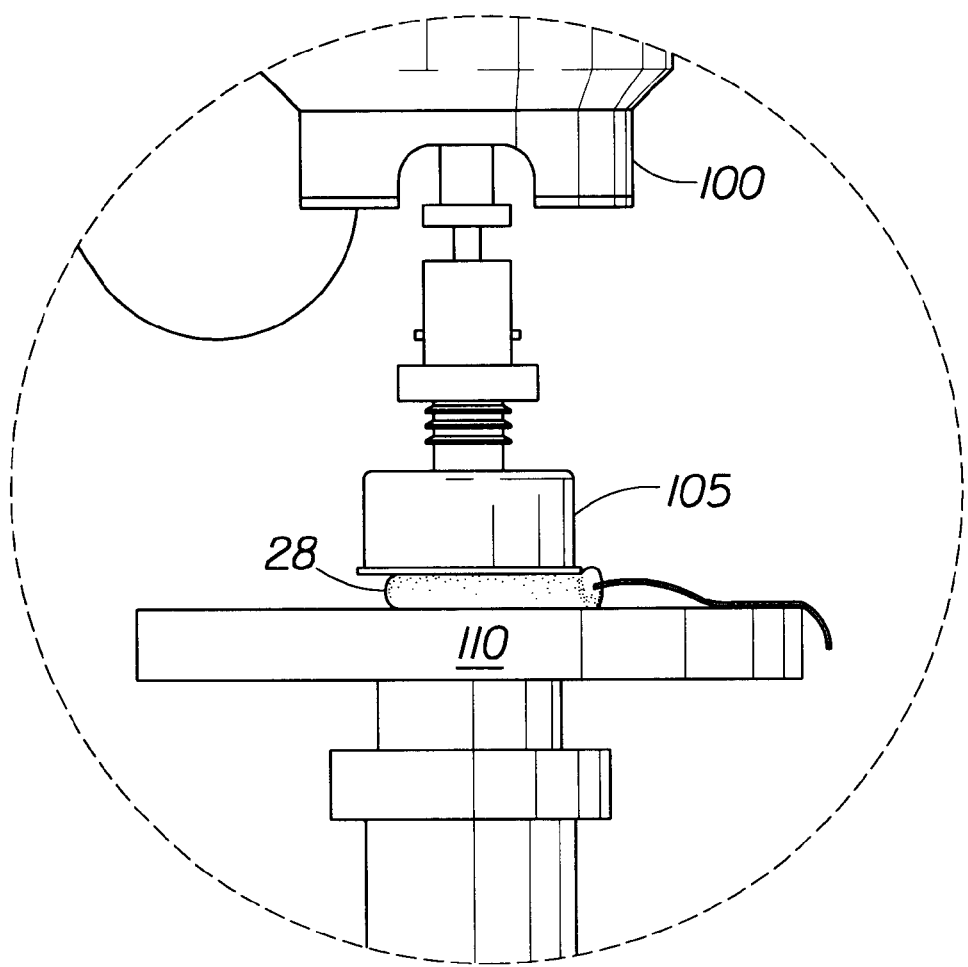
FIG. 8 is a close up front view of the apparatus shown in FIG. 8 used to conduct the Expansion Force Test.

The Expansion Force Test apparatus is shown in FIG. 7 and a close up in FIG. 8. The test method is described in greater detail below. Briefly, the apparatus comprises a load cell 100, a load cell compression platen 105, and a base compression platen 110. A tampon is placed between the load cell compression platen 105 and the base compression platen 110 and sheep blood is added at the insertion end of the tampon 28.

I. Tampon of the Present Invention

In order to better understand the present invention, a detailed description of several preferred embodiments is given. This description is intended to be by way of example, and not to limit the invention to these preferred embodiments. One of skill in the art will appreciate from this description how to make and use tampons incorporating the various features of the present invention although not every conventional feature is described in undue detail.

A. Expansion Force Characteristics

A tampon of the present invention preferably demonstrates improved expansion characteristics as compared to prior art tampons. These improved expansion characteristics may be described and measured in terms of peak force of expansion as measured in the Expansion Force Test.

A tampon of the present invention preferably exerts a greater force in the X dimension, side to side in the body, than that seen by most prior art tampons. This reduces the potential for "bypass" leakage in the early stages of tampon use by providing sufficient absorbent surface area of the tampon to contact fluid across the full width of the vaginal canal (the transverse dimension). For purposes of the present invention, this force is measured in the Expansion Force Test and recorded as the "X Dimension Force". The "X Dimension Force" corresponds to the force exerted in the X dimension by the moving X plane of the expanding tampon in the Expansion Force Test as described below.

The tampons of the present invention exert an X Dimension Force of at least about 400 grams. In another embodiment, tampons of the present invention exert X Dimension Forces of from about 600 grams to about 3000 grams, alternatively of from about 650 grams to about 1500 grams.

These improved tampons uniquely balance the improved protection gained from the increased X Dimension Force with a lower force exhibited in the Z dimension, providing increased comfort for the user. Minimizing the force exhibited in the Z dimension minimizes the pressure felt by the woman wearing the tampon since there are nerve endings along the anterior walls of the vagina (pressing against bladder) and posterior walls of the vagina (pressing against the bowels). For purposes of the present invention, this force is measured in the Expansion Force Test and recorded as the "Z Dimension Force". The "Z Dimension Force" corresponds to the force exerted in the Z dimension by the moving Z plane of the expanding tampon in the Expansion Force Test as described below.

The tampons of the present invention exert a Z Dimension Force of no greater than about 200 grams. In another embodiment, tampons of the present invention exert Z Dimension Forces of from about 30 grams to about 175 grams, alternatively from about 40 grams to about 100 grams.

As previously mentioned, the present invention uniquely balances the benefits of a high X Dimension Force relative to the Z Dimension Force. Thus, in one embodiment of the present invention, the ratio of the X Dimension Force to Z Dimension Force is from about 10 to about 50, alternatively from about 15 to about 35.

B. Tampon Materials and Components

The pledget 28, and consequently, the resulting primary absorbent member 21 of the tampon 20 may be constructed from a wide variety of liquid-absorbing materials commonly used in absorbent articles such as rayon, cotton, or comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures of these.

Preferred absorbent materials comprise cotton, rayon (including tri-lobal and conventional rayon fibers, and needle punched rayon), folded tissues, woven materials, nonwoven webs, synthetic and/or natural fibers or sheeting. The tampon and any component thereof may comprise a single material or a combination of materials. Additionally, superabsorbent materials, such as superabsorbent polymers or absorbent gelling materials may be incorporated into the tampon.

The materials for the tampon can be formed into a fabric, web, or batt that is suitable for use in the pledget by any suitable process such as airlaying, carding, wetlaying, hydroentangling, or other known techniques.

In another non-limiting preferred embodiment, the tampon pledget and resulting primary absorbent member comprise rayon, cotton, or combinations of both materials. These materials have a proven record of suitability for use in the human body. The rayon used in the tampon pledget may be any suitable type typically used in disposable absorbent articles intended for in vivo use. Such acceptable types of rayon include GALAXY Rayon (a tri-lobed rayon structure) available as 6140 Rayon from Acordis Fibers Ltd., of Hollywall, England. SARILLE L rayon (a round fiber rayon), also available from Acordis Fibers Ltd. is also suitable. Any suitable cotton material may be used in the tampon pledget. Suitable cotton material includes, long fiber cotton, short fiber cotton, cotton linters, T-fiber cotton, card strips, and comber cotton. Preferably, the cotton layers should be a scoured & bleached cotton absorbent with a glycerin finish, a leomin finish, or other suitable finish.

If the pledget of the present invention is layered, the layers may comprise different materials. For example, in one embodiment, the outer layers may comprise primarily rayon, while the intermediate layer or layers may comprise primarily cotton. Optionally, the entire pledget may comprise a uniform or non-uniform blend of materials throughout. In preferred layered embodiments, each of the layers may comprise essentially 100% of the same material, such as outer layers of 100% rayon and an intermediate layer of 100% cotton. A Super Plus absorbency tampon of the present invention may be made from a pledget comprising about 100% rayon fibers. A Super absorbency or regular absorbency tampon of the present invention may be made from a pledget comprising about 25% cotton and about 75% rayon fibers. A Junior absorbency tampon may be made from a pledget comprising about 67% cotton and about 33% rayon fibers.

The tampon of the present invention optionally includes a withdrawal cord, a secondary absorbent member, a liquid permeable overwrap material, and/or an applicator.

Withdrawal cords useful in the present invention may be made of any suitable material known in the prior art and include cotton and rayon. Additionally, the tampons of the present invention may also benefit from a secondary absorbent member. U.S. Pat. No. 6,258,075 to Taylor et al. entitled "Tampon with Enhanced Leakage Protection" describes tampons having a variety of secondary absorbent members in great detail. Any of the configurations given in this application are suitable for use as an optional secondary absorbent member in the present invention. In particular, a "fancy yarn" type of combination withdrawal cord and secondary absorbent member is suitable and one potential embodiment for a secondary absorbent member for use with the present invention. This fancy yarn may comprise a generally braided (or twisted) withdrawal cord. A conventional type of withdrawal cord (in terms of thickness, material composition, etc.) may be periodically braided with a thicker slub of absorbent fibrous material to form a "fancy yarn" type secondary absorbent member. In such an embodiment, the portion of the cord which will act as the withdrawal cord and not the secondary absorbent member may be treated to make the same non-absorbent or even hydrophobic.

Without wishing to be bound by theory, it is believed that the secondary absorbent material and the improved expansion force characteristics of the present tampon operate independently of each other and act in combination to complement the advantages of each. For example, prior to the first contact with fluid by the primary absorbent core, the secondary member is available to absorbent fluid and preferably also direct it toward the primary core. When this feature is combined with the expansion forces of the primary core, the chance that fluid will escape past the tampon without being intercepted by at least one of the primary core or secondary absorbent member is substantially reduced.

Optional overwrap materials useful herein include rayon, cotton, bicomponent fibers, polyethylene, polypropylene, other suitable natural or synthetic fibers known in the art, and mixtures thereof.

It is important for the X dimension and Z dimension of the tampon to orient in the user's body appropriately as discussed above in order to achieve the goals of the present invention. Optionally, this can be achieved through the use of a partially dimensionally oriented applicator. One suitable applicator is shown and described in U.S. Design Pat. No. 415,565 issued on Oct. 19, 1999 to Harry Hayes et al. An advantage of an applicator such as that shown in the Hayes patent is that is has dimensionality. For example, many tampon applicators have a generally cylindrical configuration and are therefore may be held in any orientation by the user. An applicator such as that described in the Hayes patent has flattened grip surfaces which dictate the orientation in which a user will hold the inserter. Therefore, the tampon may be oriented such that the primary dimension of expansion will be side to side with respect to the user's body, which may be achieved with a dimensionally oriented applicator.

However, it is also believed that the "flipping" phenomenon described above will also typically occur in the user's body, regardless of the initial orientation of the inserted tampon of the present invention. Thus, the tampon of the present invention may be inserted digitally or through the use of any applicator of the prior art. Such applicators of typically a "tube and plunger" type arrangement and may be plastic, paper, or other suitable material. Additionally, a "compact" type applicator is also suitable.

C. Absorbency

It is also desirable that tampons of the present invention be made in the absorbency ranges which are currently required by the United States Food and Drug Administration and corresponding agencies of many other governments which regulate tampon absorbency. In fact, one of the benefits of the present invention is that it provides tampons having improved protection characteristics without a corresponding increase in absorbency.

A "Super Plus" absorbency tampon should have a total absorbency as measured by the industry standard Syngyna test of 12–15 grams. A "Super" absorbency tampon should have a total absorbency as measured by the Syngyna test of 9–12 grams. A "Regular" absorbency tampon should have a Syngyna absorbency of 6–9 grams. A "Junior" absorbency tampon should have a Syngyna absorbency of less than 6 grams. Providing a tampon which properly falls within these absorbency ranges requires that the total amount and type of absorbent material be controlled.

II. Designing and Making the Tampon of the Present Invention

There are several key variables to increasing the X Dimension Force of expansion of the tampon without unduly increasing the Z Dimension Force of expansion. The compression and construction of the tampon (folded versus rolled) are important variables. The initial dimensions of the pledget, the fiber thickness and basis weights, and even the shape of the pledget may also be adjusted to change the expansion force characteristics. Specifics relative these variables are detailed below. It is expected that one of ordinary skill in the art can use the teachings herein to develop a wide array of tampons meeting the objectives of the present invention using these variables.

A key method in achieving the increased X Dimension Forces of the tampons of the present invention involves focusing the compression of the tampon in the X dimension, rather than focusing the compression radially or axially or substantially in multiple dimensions as other prior art tampons. This dimension is indicated in FIG. 2 with arrows C showing this X dimension of compression. The length of the uncompressed tampon is typically only slightly longer than the compressed tampon. This is done to keep the axial compression to a minimum so that the majority of the compression can be focused in the X dimension as mentioned above. A small amount of axial compression (in the y-direction) is beneficial to ensure good tampon head formation.

One embodiment of the present invention comprises tampons having a folded construction. "Folded construction" as used herein refers to a tampon having one or more folds in the absorbent material either prior to or as a result of compression. In one embodiment the folds are substantially uniform and complete along the entire pledget as shown in FIG. 3, although this is not necessary. In another embodiment the tampons of the present invention have at least three folds (the material changes direction three times), such as when the flat pledget is compressed and takes on a "W" shape. In yet another embodiment, the pledget is compressed, but no folds are apparent to the naked eye. Spiral wound tampons which are radially compressed such as those in the prior art are not as conducive to achieving the desired expansion forces of the present invention as they tend to expand uniformly in all directions and thus are more difficult to utilize in the present invention.

One way to minimize Z Dimension Force is to reduce the fiber weight or thickness of the fiber by distributing the amount of fiber required to meet absorbency needs across as large an area as possible prior to compressing the tampon. This can be accomplished by optimizing the width and length of the tampon pledget. For example, in one embodiment of this invention, the width of the tampon pledget was chosen to be 70 mm wide for Regular, Super, and Super Plus absorbency. In another embodiment, the width of the uncompressed tampon was chosen to be 40 mm wide for Junior absorbency. Wider uncompressed tampons widths, up to 100 mm wide, could be considered to further decrease fiber thickness, but may not appeal to users given the visual appearance of the used tampons. For example, for a tampon in the "Super Plus" or "Super" absorbency ranges, length and width dimensions of about 48 mm by about 70 mm have been found to work well. The Regular absorbency pledget may be about 50 mm in width and 40 mm in length. The Junior absorbency pledget may be about 40 mm in width and 30 mm in length.

While changing these variables, the total amount of absorbent material must be controlled in order to keep the total absorbency within the target range. A chevron shaped pledget is one manner in which both the width and the length of the pledget may be maximized without creating a pledget having an unacceptably large total volume of absorbent material. The alternative pledget shapes such as an "H" shape or bow-tie also allow for both increased total width and length of the pledget without exceeding the total desired capacity of the resulting tampon. Another benefit of chevron shaped pledgets and the alternative shapes is that these shapes result in a greater amount of absorbent material across the full width of the pledget in the middle region. This results in an absorbent core which the greatest energy of compression is stored in the middle region of the absorbent core. Consequently, the middle region tends to release the greatest amount of expansion energy and drives the X Dimension Force of the entire tampon.

The chevron shape is particularly preferred because the top portion is notched in a manner which facilitates head formation of the finished tampon. Correspondingly, the oppositely inflected bottom portion of the chevron is shaped in a manner which facilitates comfortable removal by helping to gradually spread the vaginal introitus as the tampon is removed following use.

The basis weight of the fiber in the absorbent material may also vary in order to meet the objectives of the present invention while maintaining the target absorbency range. Juniors may have basis weight ranges of from about 376 gsm to about 1100 gsm. Regulars basis weights may be from about 528 gsm to about 1163 gsm. Super tampons may have basis weights of from about 605 gsm to about 842 gsm. Super Plus could have basis weight ranges of from about 756 to about 1143 gsm. These basis weight ranges are meant to provide guidance to one of ordinary skill in the art as they design tampons of the present invention, but should not be construed to be limiting of the present invention.

Tampons of the present invention may be manufactured in a manner which is similar to that currently used for present tampons. While some equipment modification is typically required to take advantage of all features of the present invention, it is not necessary to start with a completely new manufacturing plant, for example.

Conventional compression temperatures and pressures using standard equipment such as a tampon compressor machine available from Hauni Machines, Richmond, Va., are suitable. Preferably, the dimension of compression is primarily in the widthwise dimension as described above. In particularly preferred embodiments, the pledget is subject to microwave conditioning during tampon formation. Without wishing to be bound by theory, this step is believed to heat water within the fibers of the pledget. This allows greater flexibility in the compression step. For example, if microwave conditioning is used, lower temperatures (such as room temperature or slightly elevated temperatures) during the compression step are sufficient for formation of the final tampon. It will be recognized by those of skill in the art that compression to a self sustaining form requires imparting both heat and pressure to the tampon pledget. Such heat and pressure causes the fibers to "set" and achieve this self-sustaining form subject to fluid expansion. Typically, the heat and pressure are provided simultaneously with a heated compression die. This may result in several drawbacks, however. The outer portion of the pledget which contact the compression die may tend to become scorched due to the localized heat. Additionally, the heat imparted by the die may not penetrate into the tampon in a uniform manner. The microwave conditioning overcomes these drawbacks by allowing the pressure to be imparted with a much cooler (for example, room temperature) die. The heat required is imparted by the microwaves which penetrate the tampon more uniformly and which do not tend to scorch the fibers of the tampon. This microwave conditioning is also believed to contribute the improved expansion properties associated with the present invention.

Preferably, the tampon pledget of the present invention is subject to conditioning a microwave source for about 18 seconds +/− about 5 seconds. Junior absorbency tampons may be subject to this microwave source at a power level of about 3 kW. Regular absorbency tampons are preferably subject to microwaves at a power level of about 5 kW. Super absorbency tampons are preferably subject to microwaves at a power level of about 7 kW. Super absorbency tampons are preferably subject to microwaves at a power level of about 8.5 kW.

TEST METHODS

Expansion Force Test

This test method applies to any tampon product that is capable of linear or radial expansion. This method measures the expansion force of all fluid activated cylindrical tampons.

Procedure:

1. Use the following.
    a. MTS ReNew Tensile Tester or comparable device. This machine is an Instron 5564 that has been refurbished by MTS. To obtain this unit or one like it. One would call MTS and ask for the ReNew package. All components for this package are standard so anyone ordering this package would get the same setup as everyone else.

b. 100 Newton Load Cell
c. Test Works Version 4.04
d. Compression Platens
e. 3 ml needle syringe 2. Set up apparatus as pictured in FIGS. 7 and 8
3. Place tampon on base compression platen 110.
   3.1 For non-radial or non-spiral wound tampons. Place tampon such that horizontal seam line found on the body of the tampon is parallel (and visible from the side) to the base compression platen for the X Dimension Force measurement and the horizontal seam line(s) is adjacent to the base compression platen for the Z Dimension Force measurement. In the absence of a guiding seam line, it should be obvious to one of ordinary skill in the art how to best orient the tampon to measure the X Dimension Force and Z Dimension Force data based on the construction of the tampon.
4. Lower the load cell compression platen 105 until it is in contact with the tampon.
   4.1 Ensure that there is at least 0.01 Newtons but no more then 0.05 Newtons being applied to the tampon prior to fluid introduction.
5 Load 3-milliliter needle syringe with 3 milliliters of sheep blood.
6 Click the start icon on the program and wait for "ding" from the computer
7 After the "ding" sound, proceed with fluid addition to the center of the insertion end of the tampon. Add the full 3 milliliters in the syringe to the insertion end of the tampon 28.
8 Allow the test to run for the 300 second run time. After 300 seconds the test will automatically stop as the computer program should initially be set up for 300 a second run time.
9 Repeat steps 3–8 for all remaining 4 samples.
10 The computer program which comes with the MTS ReNew tensile tester automatically graphs the force of the expanding tampon and records the peak force, or highest achieved force. It then averages the peak forces achieved for the 5 samples. This average peak force is the "X Dimension Force" or "Z Dimension Force", depending upon the orientation of the tampon in the equipment as described above.

Table 1, below presents the results using the Expansion Force Test described in the TEST METHODS section above performed on tampons of the present invention and a variety of prior art tampons. The table shows an X Dimension Force and a Z Dimension Force for various tampons as measured when injected with 3 milliliters of sheep blood.

TABLE 1

| Product | Absorbency | X Dimension Force (grams) | Z Dimension Force (grams) |
|---|---|---|---|
| A | Regular | >4996[1] | 153 |
| B | Regular | 2713 | 159 |
| C | Regular | 1139 | 84 |
| D | Super | 650 | 49 |
| E | Super Plus | 1263 | |
| O.B. ® | Regular | 1026 | 1026 |
| O.B. ® | Super | 350 | 350 |
| Playtex ® | Super | 251 | 251 |
| Playtex ® | Regular | 131 | 131 |
| Kotex ® | Super | 61 | 20 |
| Unicharm ® | Super | 146 | 45 |
| Tampax ® | Super | 115 | 43 |

[1]The chart generated by software has a limit of 5000 grams

Examples A–E are Chevron shaped pledgets formed into tampons of the present invention. The longest dimensions measured lengthwise and widthwise of the pre-compressed chevron pledgets are provided below in millimeters, along with their absorbent matter make-up A=40×30, top region length*=12 mm, 50% cotton, 50% rayon, basis weight=1533 gsm
B=55×38, top region length*=12 mm, 50% cotton, 50% rayon, basis weight=880 gsm
C=70×46, top region length*=12 mm, 50% cotton, 50% rayon, basis weight=571 gsm
D=70×46, top region length*=18 mm, 25% cotton, 75% rayon, basis weight=788 gsm
E=70×48, top region length*=18 mm, 100% rayon, basis weight=1143 gsm

*Measured Top Region 6 as shown on FIGS. 2, 4, and 5.

| Absorbent Material Shape | Absorbency | Tampon Dimensions (length (mm) × width (mm)) | Tampon Top Region Length (mm)[1] | % Rayon/ % Cotton | Basis Weights (gsm) |
|---|---|---|---|---|---|
| Chevron | Junior | 40 × 46 | 12 | 75%/25% | 658 |
| Chevron | Junior | 70 × 46 | 12 | 75%/25% | 376 |
| Chevron | Junior | 40 × 46 | 12 | 100% rayon | 777 |
| Chevron | Junior | 70 × 46 | 12 | 100% rayon | 444 |
| Chevron | Junior | 40 × 30 | 12 | 67%/33% | 110 |
| Chevron | Regular | 40 × 46 | 12 | 50%/50% | 1163 |
| Chevron | Regular | 60 × 46 | 12 | 50%/50% | 667 |
| Chevron | Regular | 70 × 46 | 12 | 75%/25% | 528 |
| Chevron | Regular | 70 × 46 | 12 | 100% cotton | 665 |
| Chevron | Super | 70 × 48 | 18 | 75%/25% | 756 |
| Chevron | Super | 70 × 50 | 18 | 75%/25% | 726 |
| Chevron | Super | 70 × 60 | 18 | 75%/25% | 605 |
| Chevron | Super | 70 × 46 | 18 | 50%/50% | 842 |
| Chevron | Super | 70 × 48 | 18 | 50%/50% | 807 |
| Chevron | Super Plus | 70 × 48 | 18 | 75%/25% | 970 |
| Chevron | Super Plus | 70 × 48 | 18 | 100% rayon | 1143 |
| Chevron | Super Plus | 70 × 62 | 18 | 75%/25% | 756 |
| Bow-tie | Junior | 70 × 58 | 12 | 67%/33% | 410 |
| Bow-tie | Regular | 70 × 58 | 12 | 50%/50% | 571 |
| Bow-tie | Super | 70 × 66 | 18 | 75%/25% | 864 |
| Bow-tie | Super Plus | 70 × 66 | 18 | 100% rayon | 1306 |
| Rectangle | Junior | 70 × 58 | | 67%/33% | 325 |
| Rectangle | Regular | 70 × 58 | | 50%/50% | 453 |
| Rectangle | Super | 70 × 66 | | 75%/25% | 550 |
| Rectangle | Super Plus | 70 × 66 | | 100% rayon | 831 |
| $H^2$ | Junior | 70 × 58 | 12 | 67%/33% | 395 |
| $H^2$ | Regular | 70 × 58 | 12 | 50%/50% | 551 |
| $H^2$ | Super | 70 × 66 | 18 | 75%/25% | 718 |
| $H^2$ | Super Plus | 70 × 66 | 18 | 100% rayon | 1085 |

[1]Measured Top Region 6 as shown on FIGS. 2, 4, and 5.
[2]The gap width is 30 mm for each "H" example.

The disclosures of all patents, patent applications (and any patents which issue thereon) referred to in this specification (including those listed in the Cross Reference to Related Applications Section) are hereby incorporated by reference as if fully set forth herein. While particular embodiments of the present invention have been illustrated and described, it would be obvious to those skilled in the art that various other changes and modifications can be made without departing from the spirit and scope of the invention.

What is claimed is:

1. An absorbent tampon comprising:
   a mass of absorbent material which is fluid expanding,
   said tampon has a substantially planar configuration when said fluid contacts said tampon,
   said tampon exerting an X Dimension Force of at least about 400 grams, and
   a Z Dimension Force of less than about 200 grams.

2. The absorbent tampon of claim 1 wherein the Z Dimension Force is from about 40 grams to about 100 grams.

3. The absorbent tampon of claim 2 having an absorbent capacity as measured by the syngyna test of between about 6 to about 9 grams.

4. The absorbent tampon of claim 2 having an absorbent capacity as measured by the syngyna test of between about 9 to about 12 grams.

5. The absorbent tampon of claim 2 having an absorbent capacity as measured by the syngyna test of between about 12 to about 15 grams.

6. The absorbent tampon of claim 2 having an absorbent capacity as measured by the syngyna test of between about 15 to about 18 grams.

7. The absorbent tampon of claim 2 having an absorbent capacity as measured by the syngyna test of less than about 6 grams.

8. The absorbent tampon of claim 1 wherein the X Dimension Force is greater than about 600 grams and the Z Dimension Force is less than about 100 grams.

9. The absorbent tampon of claim 1 wherein the absorbent material is folded.

10. The absorbent tampon of claim 9 wherein the absorbent material has at least three folds.

11. The absorbent tampon of claim 1 housed in a directional applicator.

12. The absorbent tampon of claim 1 having a secondary absorbent member.

13. An absorbent tampon comprising:
    a mass of absorbent material which is fluid expanding,
    said tampon exerting an X Dimension Force of at least about 400 grams and a Z Dimension Force;
    wherein the ratio of the X Dimension Force to the Z Dimension Force is from about 10 to about 50.

14. The absorbent tampon of claim 13 wherein the absorbent material is a chevron shape prior to compression.

15. The absorbent tampon of claim 13 having an absorbent capacity as measured by the syngyna test of between about 9 to about 12 grams.

16. The absorbent tampon of claim 13 wherein the tampon has a folded construction.

17. An absorbent tampon comprising:
    a mass of absorbent material which is fluid expanding,
    said tampon exerting a Z Dimension Force of from about 30 grams to about 200 grams and an X Dimension Force;
    wherein the ratio of the X Dimension Force to the Z Dimension Force is from about 10 to about 50.

18. The absorbent tampon of claim 17 wherein the ratio of the X Dimension Force to the Z Dimension Force is from about 15 to about 35.

19. The absorbent tampon of claim 18 wherein the absorbent material has at least three folds.

20. The absorbent tampon of claim 17 wherein the tampon undergoes minimal axial compression.

* * * * *